US007377169B2

(12) United States Patent
Myers et al.

(10) Patent No.: US 7,377,169 B2
(45) Date of Patent: May 27, 2008

(54) APPARATUS AND METHODS FOR ACOUSTICALLY DETERMINING FLUID PROPERTIES WHILE SAMPLING

(75) Inventors: Michael Tolbert Myers, Sugarland, TX (US); Donald Keith Love, Humble, TX (US); Willem J. M. Epping, Houston, TX (US); Mohamed Naguib Hashem, Mandeville, LA (US)

(73) Assignee: Shell Oil Company, Houston, TX (US)

( * ) Notice: Subject to any disclaimer, the term of this patent is extended or adjusted under 35 U.S.C. 154(b) by 122 days.

(21) Appl. No.: 10/821,767

(22) Filed: Apr. 9, 2004

(65) Prior Publication Data

US 2005/0223808 A1   Oct. 13, 2005

(51) Int. Cl.
*G01N 29/02* (2006.01)
*E21B 44/00* (2006.01)

(52) U.S. Cl. .................. 73/587; 73/152.18; 73/152.28; 73/152.46

(58) Field of Classification Search .................. 73/587, 73/597, 64.53, 61.45, 61.75, 61.79, 24.01, 73/24.04, 152.05, 152.55, 152.18, 152.28, 73/152.32, 152.46, 152.47

See application file for complete search history.

(56) References Cited

U.S. PATENT DOCUMENTS

| 4,142,414 | A | * | 3/1979 | Cosentino ...................... 73/216 |
| 4,419,880 | A | * | 12/1983 | Hanowich ................... 73/1.22 |
| 4,991,124 | A | * | 2/1991 | Kline ............................. 702/50 |
| 5,477,101 | A | * | 12/1995 | Ounadjela ................... 310/334 |
| 5,494,102 | A | * | 2/1996 | Schulte ..................... 166/105.6 |
| 5,515,733 | A |   | 5/1996 | Lynnworth ............... 73/861.27 |
| 5,622,223 | A | * | 4/1997 | Vasquez ..................... 166/264 |
| 5,661,241 | A | * | 8/1997 | Harth et al. ................... 73/622 |
| 5,708,191 | A |   | 1/1998 | Greenwood et al. ........ 73/32 A |
| 5,741,962 | A | * | 4/1998 | Birchak et al. ........... 73/152.16 |
| 5,741,971 | A | * | 4/1998 | Lacy ............................ 73/597 |
| 5,886,250 | A |   | 3/1999 | Greenwood et al. ........ 73/32 A |
| 5,900,546 | A | * | 5/1999 | Wilkins ..................... 73/290 V |
| 6,176,323 | B1 | * | 1/2001 | Weirich et al. ............... 175/40 |
| 6,467,544 | B1 | * | 10/2002 | Brown et al. ............... 166/264 |
| 6,490,916 | B1 | * | 12/2002 | Goodwin et al. ........ 73/152.58 |
| 6,508,133 | B1 | * | 1/2003 | Adachi et al. ........... 73/861.18 |

(Continued)

FOREIGN PATENT DOCUMENTS

| EP | 1081471 A1 | 7/2000 |
| WO | 95/19559 | 7/1995 |
| WO | WO 02/057596 A1 | 7/2002 |
| WO | WO 02/057597 A1 | 7/2002 |

OTHER PUBLICATIONS

Search Report dated Jun. 4, 2005.
Written Opinion dated Sep. 4, 2004.

(Continued)

*Primary Examiner*—Hezron E. Williams
*Assistant Examiner*—Jacques M. Saint-Surin (57) ABSTRACT

An apparatus and methods for acoustically analyzing a fluid sample and determining one or more properties of the sample are disclosed by the present invention. The apparatus comprises a chamber, a transmitter positioned within the chamber for transmitting an acoustic signal through the fluid, a reflector movably positioned within the fluid inside the chamber for reflecting the acoustic signal, and a receiver positioned within the chamber for detecting reflections of the acoustic signal. The methods employ the use of a transmitter, a reflector movably positioned within the fluid inside the chamber, and a receiver to characterize the fluid sample based on one or more of its acoustic properties.

66 Claims, 5 Drawing Sheets

U.S. PATENT DOCUMENTS

| | | | | |
|---|---|---|---|---|
| 6,508,134 | B1* | 1/2003 | Feller | 73/861.27 |
| 6,640,625 | B1* | 11/2003 | Goodwin | 73/152.05 |
| 6,683,681 | B2 | 1/2004 | DiFoggio et al. | 356/128 |
| 6,734,675 | B2* | 5/2004 | Fanini et al. | 324/339 |
| 6,820,462 | B2* | 11/2004 | Cardelius | 73/24.01 |
| 6,912,891 | B2* | 7/2005 | Coupland et al. | 73/64.53 |
| 6,988,547 | B2* | 1/2006 | Goodwin et al. | 166/53 |
| 7,024,917 | B2* | 4/2006 | DiFoggio | 73/30.01 |
| 7,075,215 | B2* | 7/2006 | Yogeswaren | 310/334 |
| 7,091,719 | B2* | 8/2006 | Freedman | 324/303 |
| 7,124,819 | B2* | 10/2006 | Ciglenec et al. | 166/264 |
| 2003/0066646 | A1 | 4/2003 | Shammai et al. | 166/264 |
| 2003/0176789 | A1 | 9/2003 | Kaplan | 600/438 |
| 2004/0207403 | A1* | 10/2004 | Fanini et al. | 324/339 |
| 2005/0204808 | A1 | 9/2005 | DiFoggio | 73/152.58 |

OTHER PUBLICATIONS

Greenwood, Margaret S., Skorpik, James R., Bamberger, Judith Ann, *On-line Sensor for Density and Viscosity Measurement of a Liquid or Slurry for Process Control in the Food Industry*, 1999, 6 pages, presentation at the American Institute of Chemical Engineers Conference on Food Engineering '99 Sensors and Controls technical session (T3014-63f) (Unpublished).

Author Unspecified, *In Situ Sensor Development: Ultrasonic Density Measurement Probe*, Aug. 1996, pp. 69-72, *Characterization, Monitoring, and Sensor Technology Crosscutting Program*—Aug. 1996.

Author Unspecified, *Ultrasonic Density Measurement with acoustic reference path*, undated, one page printout from the website of the Institute for Micro und Sensor Systems, www.uni-magdeburg.de/imos.

Shammai, Michael; Shaw, Andy; DiFoggio, Rocco; Gordon, Bob; Ferworn, Kevin; and Ford, John, *Improving Formation Sampling and Testing Efficiency—Tomorrow's In-Situ PVT Laboratory*, Nov. 13-15, 2002, pp. 1-12, presentation made at the 14th Annual Deep Offshore Technology International Conference, Nov. 13-15, 2002.

Higuti, Ricardo Tokio and Adamowski, Julio Cezar, *Ultrasonic Densitometer Using a Multiple Reflection Technique*, Sep. 2002, pp. 1260-1268, *IEEE Transactions on Ultrasonics, Ferroelectrics, and Frequency Control*, vol. 49, No. 9, Sep. 2002.

Adamowski, J. C., Buiochi, F.; Simon, C., Silva, E.C.N., and Sigelmann, R., *Ultrasonic measurement of density of liquids*, Jan. 1995, pp. 354-361, *J. Acoust. Soc. Amer.*, vol. 97, Jan. 1995.

Definition of Sampling, Merriam-Webster Online Dictionary, http://www.m-w.com/cgi-bin/dictionary, p. 1.

Definition of Sample. Merriam-Webster Online Dictionary, http://www.m-w.com/dictionary/sample, p. 1.

SA-SH Glossary, Offshore Minerals Management Glossary, http://www.mms.gov/glossary/sa-sh.htm, pp. 1-2.

* cited by examiner

APPARATUS AND METHODS FOR ACOUSTICALLY DETERMINING FLUID PROPERTIES WHILE SAMPLING

CROSS-REFERENCE TO RELATED APPLICATIONS

Not applicable.

STATEMENT REGARDING FEDERALLY SPONSORED RESEARCH

Not applicable.

FIELD OF THE INVENTION

The present invention relates to an apparatus and method for acoustically analyzing a fluid sample. More particularly, the present invention relates to an apparatus and methods for acoustically determining various properties of a fluid sample at in situ conditions.

BACKGROUND OF THE INVENTION

Density is the fundamental physical property that can be used alone or in conjunction with other properties to characterize fluids in many industrial processes, such as in the petroleum, chemical and food industries. Laboratory measurements of density can reach accuracies of 0.01% or less, if sufficient care is taken during the transportation and analysis of the fluid sample.

Various methods of measuring the density of a fluid have been proposed however, are not well suited for in situ use. For example, many conventional densitometers are limited by their physical construction if the acoustic transducer(s) are affixed directly to the fluid sample chamber. When the chamber is subjected to extreme in situ pressure, the chamber dimensions may be affected thus, requiring recalibration of the device with each change in the fluid sample pressure. The net effect is a greater degree of uncertainty in the density measurements taken. Various other density measurement devices have been developed to maximize precision while reducing material complexity as discussed in Vol. 49, No. 9, of the September 2002 issue of *IEEE Transactions On Ultrasonics, Ferroelectrics, and Frequency Control*, titled *Ultrasonic Densitometer Using a Multiple Reflection Technique* by Ricardo Tokio Higuti and Julio Cezar Adamowski. The accuracy of these devices, however, is also limited by temperature and pressure conditions of the fluid sample, which may alter the dimensions of the device. As a result, these devices may require excessive recalibration with each fluid sample and/or may present unacceptable results at extreme pressures.

Another common ultrasonic method used to measure the density of fluids is based on the measurement of the reflection coefficient at the interface between a reference material and the fluid sample as more fully described in U.S. Pat. Nos. 5,708,191 and 5,886,250. The '191 and '250 patents each describe methods for determining the density of a fluid sample by means of a material wedge positioned in the fluid. The material properties of the wedge are limited to materials having an acoustic impedance no greater than eleven (11) times that of the fluid sample. These methods are therefore, limited by their material requirements, which may be wholly inappropriate for certain fluids and at in situ conditions.

In the petroleum industry, reservoirs are usually several thousands of feet from the earth's surface and are typically under extreme pressures reaching several tens of thousands of pounds per square inch. Geothermal temperatures at these depths are on the order of 250° F. or more. Most conventional tools and associated methods are therefore, either inappropriate or impractical for taking density measurements of formation fluid samples from the earth at in situ temperatures and pressures. Consequently, formation fluid samples taken by conventional means, such as by a wireline device, are normally shipped to a laboratory where, under controlled conditions mimicking in situ pressure and temperature, density and other properties may be determined. The fluid properties may substantially impact decisions as to whether production may be economically achieved and, if so, the duration, expense and unit price of such production.

Transfer of the formation fluid sample to the surface environment, however, may induce several irreversible changes in the fluid sample. For example, during the rise of a fluid sample to the surface, both pressure and temperature drop substantially. Pressure and temperature changes may cause certain components of the fluid sample to irreversibly precipitate from solution and/or colloidal suspension, causing the fluid sample to be underestimated by surface testing. Production events such as paraffin or asphaltene deposition may also be avoided by preservation of the formation fluid sample at in situ conditions. For these reasons, preservation of the in situ state of a fluid sample during testing is preferred over mimicking in situ conditions.

Figure 1:
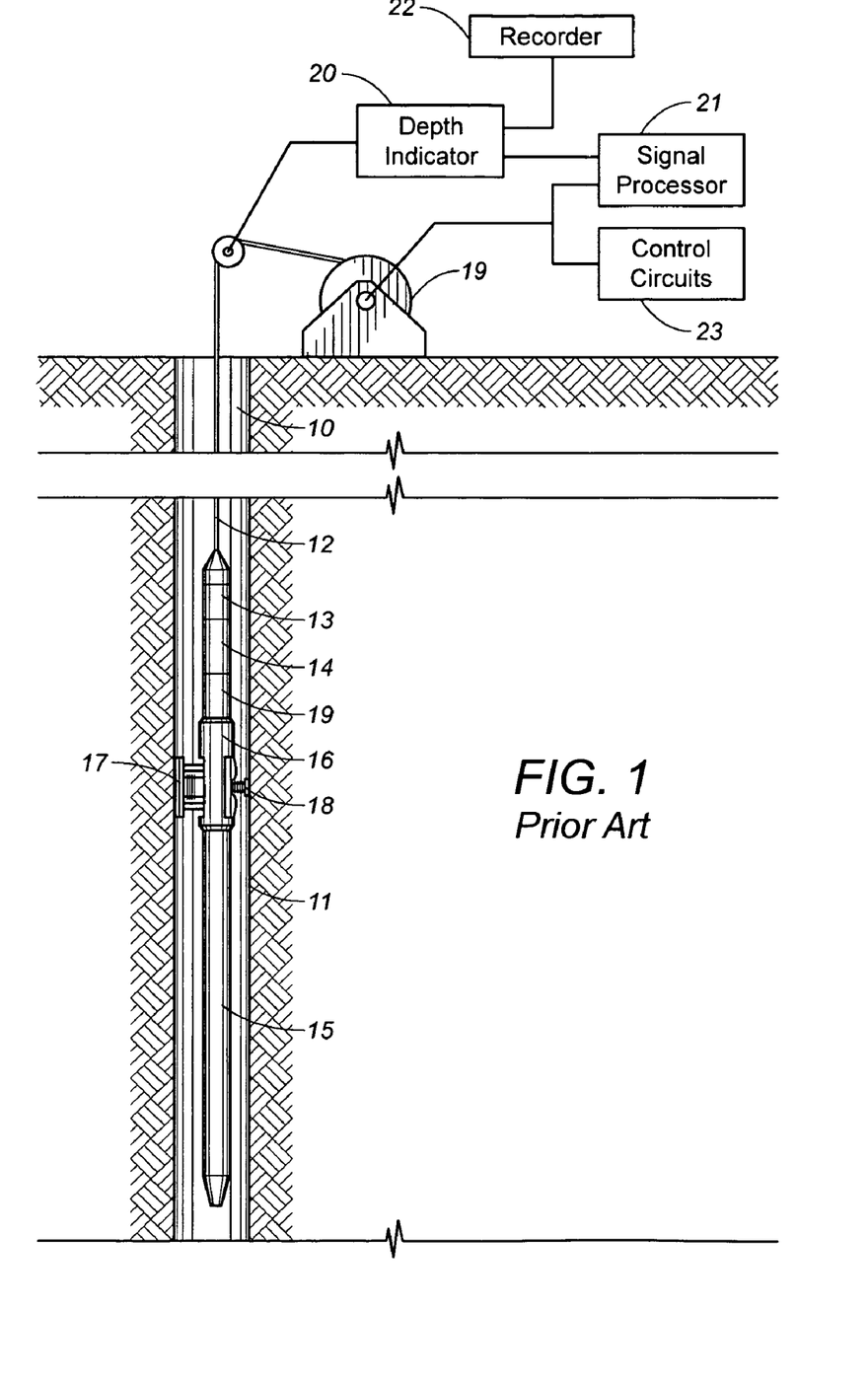
FIG. 1 is a schematic illustration of the formation fluid sampler and cooperative devices illustrated in FIG. 1 of the '112 application.
Figure 2:
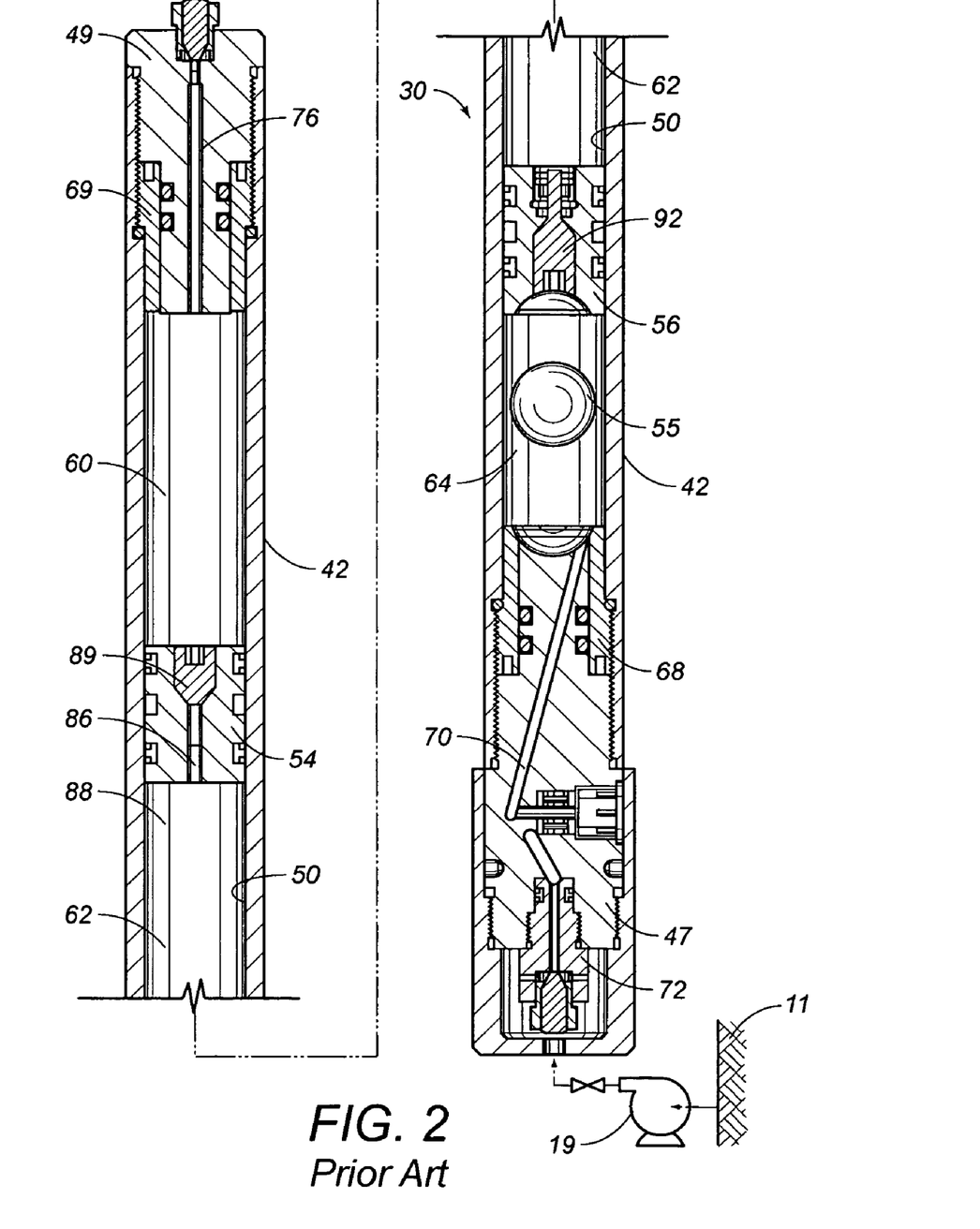
FIG. 2 is a schematic sectional view of one embodiment of a formation sampling tool described in reference to FIG. 2 of the '112 application.

One example of a conventional wireline sampling device that addresses this issue is illustrated in U.S. patent application Ser. No. 10/242,112, published on Apr. 10, 2003 and incorporated herein by reference. The '112 application describes a device or tool for maintaining the single phase integrity of a deep formation well sample that is removed to the surface for testing. Referring to FIG. 1 of the '112 application, the sampling and measuring instrument (tool) 13 is positioned within borehole 10 by winding or unwinding cable 12 from hoist 19, around which cable 12 is spooled. Depth information from depth indicator 20 is coupled to signal processor 21 and recorder 22 when instrument 13 is disposed adjacent an earth formation of interest. Electrical control signals from control circuits 23 are transmitted through electrical conductors contained within cable 12 to instrument 13. The sampling mechanism or tool 13 is comprised of a hydraulic power system 14, a fluid sample storage section 15, and a sampling mechanism section 16. Sampling mechanism 16 includes a selectively extensible well wall engaging pad member 17, a selectively extensible fluid admitting sampling probe member 18, and bi-directional pumping member 19. Within the sample storage section 15 are one or more sample accumulation chambers 30. FIG. 2 schematically illustrates a fundamental configuration of accumulation chamber 30. While improving on the preservation of in situ conditions of the fluid sample, this tool does not address other problems associated with analyzing the formation fluid sample at a lab, such as:

i) limitations on the available number of fluid samples using conventional wireline devices;

ii) transport delays;

iii) deterioration of fluid samples by improper handling and conditioning;

iv) delayed use of test results for field appraisal (hydrocarbon potential) and well planning;

v) limitations on lab conditions and instruments; and vi) export restrictions.

Some fluid properties, however, may be analyzed in situ as illustrated in U.S. Pat. No. 6,683,681 B2, issued Jan. 27, 2004 and incorporated herein by reference. The '681 patent describes an apparatus and method for measuring the refractive index of fluids along a continuum, for measuring attenuated reflectance spectra, and for interpreting the measurements made with the apparatus to determine a variety of formation fluid parameters. This device, however, may require more complex and sophisticated equipment than is necessary or desired to determine certain physical parameters of a formation fluid sample-particularly acoustic velocity.

Other conventional techniques may propose an estimated or simulated pressure, volume and temperature (PVT) of the fluid sample based upon pressure gradients and geochemical parameters of the fluid sample in situ. Conventionally proposed index and/or estimate techniques may be limited, however, by the physical properties of the fluid sample that must be analyzed and their accuracy, which may depart as much as 10-15% from laboratory values.

There is, therefore, a need for a device capable of accurately determining fluid properties such as velocity, volume, density, compressibility and viscosity with nominal calibration at in situ conditions. Additionally, there is a need for a device that is simple, efficient, and easily incorporated into conventional wireline fluid sampling tools or any downhole sampling device. Finally, such a device should also be capable of analyzing similar fluid properties in other industries.

SUMMARY OF THE INVENTION

The present invention therefore, provides an apparatus for acoustically analyzing a fluid sample comprising a chamber, a transmitter positioned within the chamber for transmitting an acoustic signal through the fluid, a reflector movably positioned within the fluid for reflecting the acoustic signal, and a receiver positioned within the chamber for detecting reflections of the acoustic signal.

In another embodiment, the present invention provides a method for acoustically analyzing a fluid sample in a chamber using a transmitter, a substantially stationary reflector positioned within the fluid, and a receiver. The method comprises the steps of transmitting an acoustic signal from the transmitter through the fluid and detecting reflections of the acoustic signal from the reflector at the receiver. In another embodiment, the present invention provides a method for acoustically analyzing a fluid sample in a chamber using a transmitter, a reflector moveably positioned within the fluid and a receiver. The method comprises the steps of transmitting acoustic signals from the transmitter through the fluid and detecting reflections of the acoustic signals from the reflector at the receiver as the reflector moves.

BRIEF DESCRIPTION OF THE DRAWINGS

The present invention is described with reference to the accompanying drawings in which, like reference numbers indicate identical or functionally similar elements.

DETAILED DESCRIPTION OF THE PREFERRED EMBODIMENTS

In the oil and gas industries, large sums of money are spent in order to locate hydrocarbon deposits and determine the hydrocarbon production potential of a known reservoir. In this quest to locate hydrocarbons and estimate their potential, exploration wells are utilized. These wells may also be used to determine other properties of the hydrocarbons, which are present. Often the design specification and material costs used to construct these wells is dependent on the properties of the hydrocarbons such as gas/oil ratios, viscosity, compressibility, bubble point pressure, volume, velocity and density.

Conventionally, wireline formation testing tools, such as the Baker Atlas Reservoir Characterization Instrument illustrated in FIG. 1 may be used to sample formation fluids drawn from a formation through an exploration well. Initially, fluids that are withdrawn may be highly contaminated by filtrates of the fluids ("muds") that were used during drilling. To obtain samples that are sufficiently clean (usually less than 10% contamination) so that the sample will provide meaningful lab data concerning the formation, formation fluids are generally pumped from the wellbore while clean up is being monitored in real time. Then, these withdrawn fluids can be collected downhole in tanks for subsequent laboratory analysis at the surface. Measuring instruments in the wellbore environment must therefore, operate within a limited space and under extreme conditions, including elevated pressures, temperatures, vibration and shock.

The present invention proposes such an instrument for determining one or more properties of a fluid sample, which may be used in a laboratory environment and/or incorporated into conventional wireline fluid sampling tools for in situ use.

Figure 3:
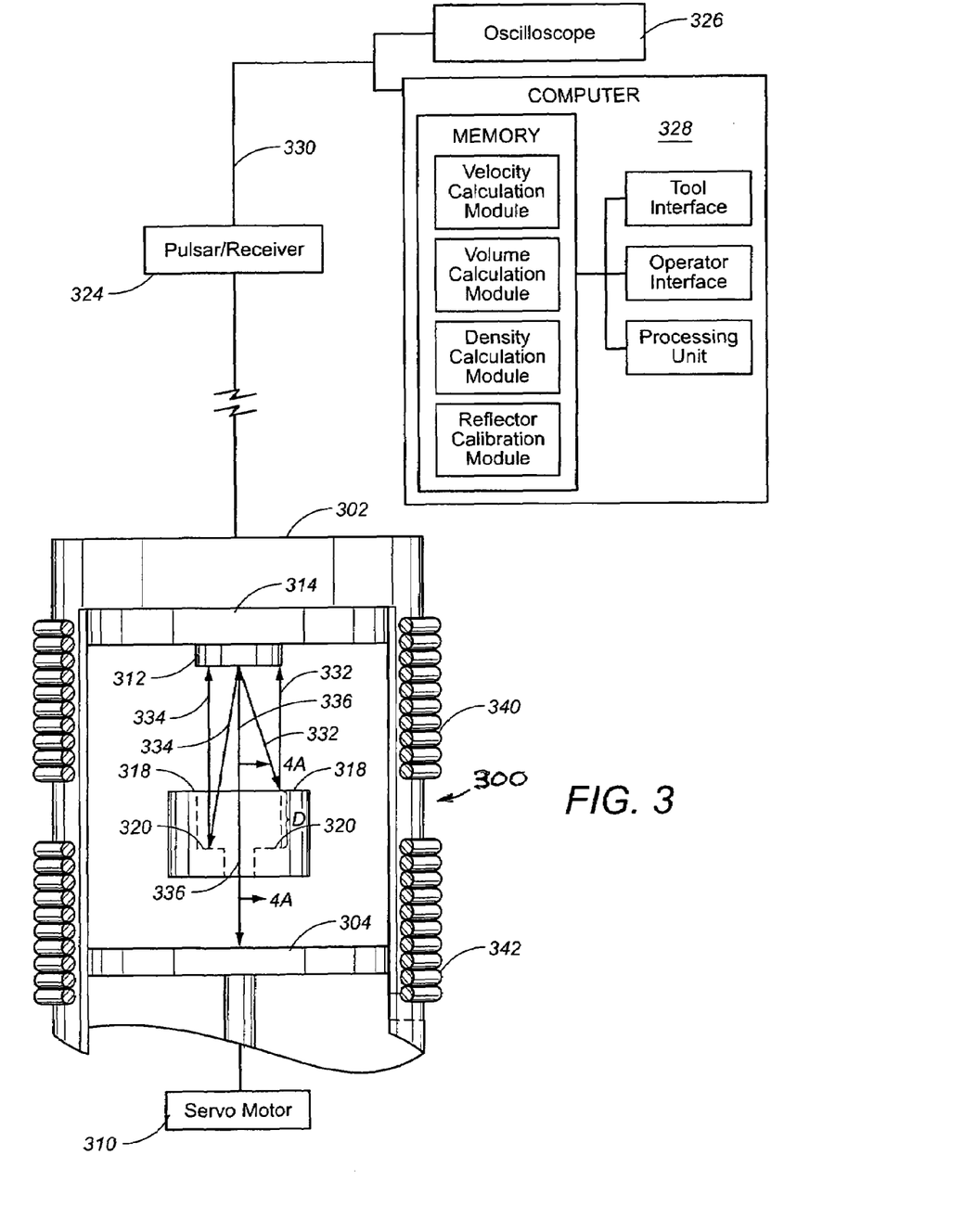
FIG. 3 is a partial elevational view illustrating one embodiment of the present invention and its related components.

Referring now to FIG. 3, one embodiment of an apparatus is illustrated for acoustic analysis of a fluid sample. The apparatus comprises a chamber 300 for the sample fluid. The chamber 300 comprises a sealed first end 302, a piston 304 slidably disposed within a second end 306 of the chamber 300 and a conduit 308 for introducing the fluid into the chamber 300. Those of ordinary skill in the art will appreciate that the conduit 308 is merely one of many components that may be employed to charge the chamber 300 with a fluid sample to a predetermined pressure. The same conduit 308, or another conduit (not shown) may be used to safely and controllably discharge the fluid sample from chamber 300.

A servomotor 310 may be coupled to the piston 304 by one or more machine screws and is computer-controlled through a power/data cable 330 for driving the piston 304 and varying at least one of the pressure and temperature of the fluid within the chamber 300. The piston 304 and chamber 300 may be thermally insulated to substantially maintain the pressure and/or temperature of the fluid within the chamber 300.

A transmitter and a receiver are positioned within the chamber 300 for transmitting an acoustic signal through the fluid and detecting reflections of the acoustic signal, respectively. The transmitter and receiver may be rigidly mounted to the chamber 300 near the first end 302 and on the piston 304, respectively, or vice versa. In one embodiment, the transmitter and the receiver are embodied in a single piezoelectric transducer 312, which is supported within the fluid in the chamber 300 by a static piston 314 rigidly mounted to the chamber 300 near the first end 302. A 0.5" diameter 1 MHz Valpey Fisher compressional wave acoustics transducer is preferred, however, any transducer may be used that emits an acoustic signal in a range from about 0.5 MHz to about 10 MHz. Because the transducer 312 is freely suspended in the fluid sample within the chamber 300, there are no interface corrections required between the transducer 312 and the fluid sample. The transducer may, alternatively, be positioned on the piston 304, which permits continuous monitoring of the acoustic reflections compared to pressure variations starting from below reservoir pressure up to the pressure limitations of the chamber 300. Other benefits may include early indication of sand entry and monitoring pump efficiency.

Figure 4A:
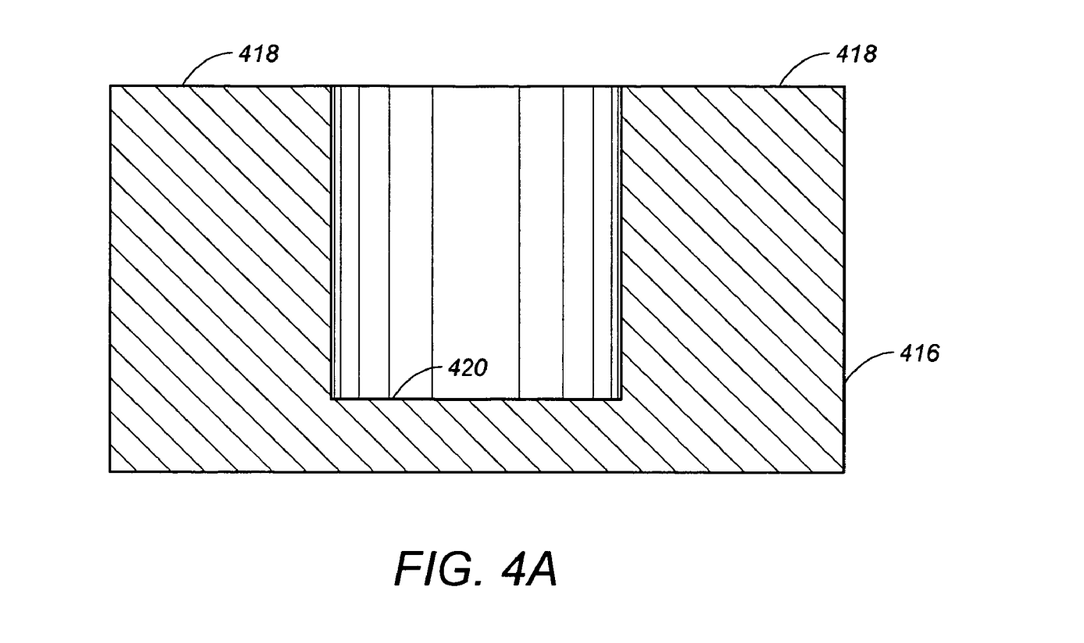
FIG. 4A is a cross-sectional side view of the reflector illustrated in FIG. 3 along line 4A-4A.
Figure 4B:
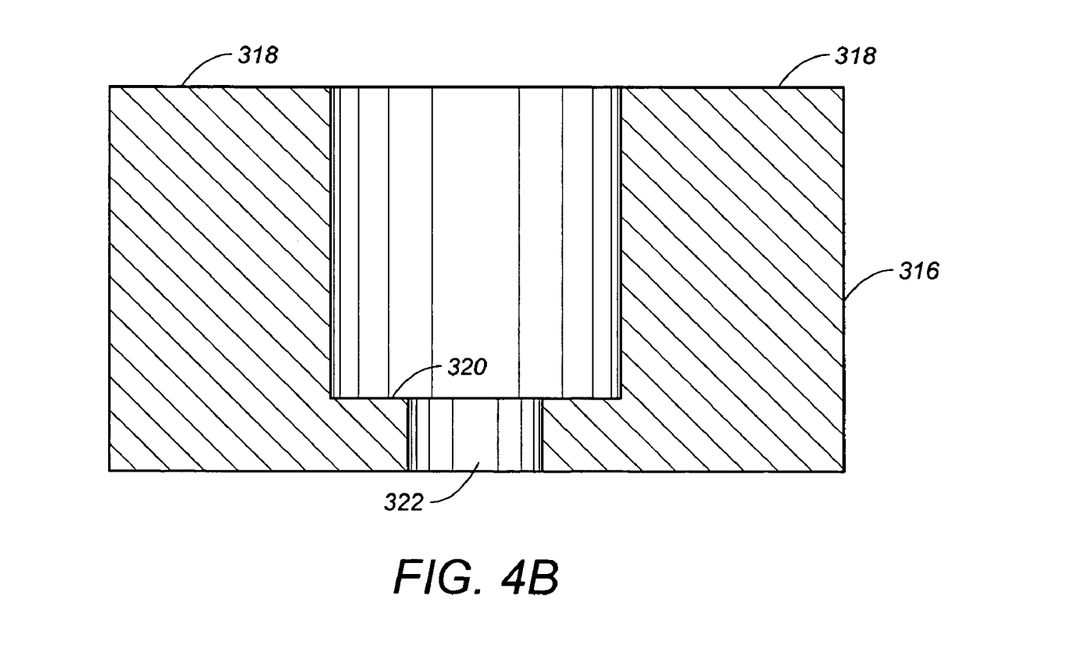
FIG. 4B is a cross-sectional side view of another embodiment of the reflector shown in FIG. 4A.

A reflector 316 is movably positioned within the fluid inside the chamber 300 for reflecting the acoustic signal and mixing the fluid. The reflector 316 is therefore, positioned opposite the transducer 312 relative to the piston 304. The reflector may be ring-shaped as illustrated in FIGS. 3 and 4A or, alternatively, shaped like a disc as illustrated in FIG. 4B. In either embodiment, the reflector 316 comprises a first reflective surface 318 and a second reflective surface 320. The reflector 316 also comprises a longitudinal opening 322 passing through the reflector 316. The reflector 316 is substantially cylindrical in shape however, may comprise alternative shapes depending on the material requirements and design of the chamber 300. The longitudinal passage 322 through the reflector 316 is stepped to create the second reflective surface 320 within the reflector 316. A distance (D) is therefore, known upon the construction of the reflector 316. The reflector 316 may be manufactured from any material having a sufficiently low coefficient of thermal expansion and a high bulk modulus including, for example, any non-corrosive metal or metal alloy to reduce any variation in distance (D) when the material is subjected to extreme temperatures and pressures within the chamber 300.

Because the reflector 316 is freely suspended inside the chamber 300 and immersed in the fluid sample, it experiences only the isostatic compression of the fluid. Unlike the remainder of the components, it experiences no differential stresses. The reflectors bulk strain as a function of temperature and pressure is therefore, easily calibrated from its known material properties by techniques well known in the art. Thus, the material properties of the reflector 316 mitigate any variation in the distance (D) as the material is subjected to extreme temperatures and pressures within the chamber 300.

In FIG. 4B, an alternative embodiment of the reflector is illustrated. The reflector 416, like reflector 316, is substantially cylindrical however, forms a disc without the longitudinal passage 322 illustrated in FIG. 4A. The reflector 416 also comprises a first reflective surface 418 and a second reflective surface 420. The reflector 416 may also be manufactured from any material having a sufficiently low coefficient of thermal expansion and high bulk modulus.

A square wave pulsar/receiver 324 is electrically coupled with the transducer 312 through cable 330 for driving the same and processing the reflections of the acoustic signal. A Panametrics Model 5077PR square-wave pulsar/receiver is preferred, however, other commercially available pulsar/receivers may also be used. The pulsar/receiver 324 may be electrically coupled with the transducer 312 by means of high pressure electrical feed through connectors available from Kemlon Products and Development Company in Houston, Tex. The pulsar/receiver 324 preferably drives the transducer 312 in the pulse/echo mode. The pulsar/receiver 324 provides the radio frequency (RF) output and may be connected to an oscilloscope 326 through cable 330 for imaging the reflections of the acoustic signal. Any commercially available oscilloscope may be used such as the Agilent Technologies 54657A 500 MHz oscilloscope.

A computer 328 may be used to operate the servomotor 310, pulsar/receiver 324 and oscilloscope 326. The computer 328 may include components comprising a processing unit, an operator interface, and a tool interface. The computer 328 may also comprise memory including a velocity calculation module, a volume calculation module, a density calculation module, and a reflector calibration module. The computer 328 may further comprise a bus that couples various system components including the memory to the processing unit. The computer 328 is only one example of a suitable computing environment and is not intended to suggest any limitation as to the scope of use or functionality of the invention. Furthermore, the computer 328 and oscilloscope 326 may be located at the surface of an earth formation when the apparatus is used within a wellbore and connected to the surface by means of a cable 330. Alternatively, the computer 328 may have an oscilloscope, precluding the need for a separate oscilloscope 326. Cable 330 may be constructed of any known type of cable for transmitting signals and/or power between the computer 328, the pulsar/receiver 324 and/or the servomotor 310. Alternatively, the computer 328 may be positioned below the surface, incorporated in the apparatus, positioned at a remote location, or positioned at any other convenient place.

The memory preferably stores various modules, which may be described as program modules containing computer-executable instructions executed by the computer 328. The reflector calibration module contains computer-executable instructions necessary to calibrate the reflector distance (D). The velocity calculation module includes computer-executable instructions necessary to calculate the acoustic velocity of the fluid sample at an in situ pressure. The volume calculation module includes computer-executable instructions necessary to calculate the volume of the fluid in the chamber 300. And, the density calculation module includes computer-executable instructions necessary to calculate a density of the fluid. These program modules will be further described below in conjunction with the method of using the apparatus.

Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer storage media including memory storage devices.

Although the computer 328 is shown as having a generalized memory, it may include a variety of computer-readable media. By way of example, and not limitation, computer-readable media may comprise computer storage media and communication media. The memory may include computer storage media in the form of volatile and/or nonvolatile memory such as a read only memory (ROM) and random access memory (RAM). A basic input/output system (BIOS), containing the basic routines that help to transfer information between elements within computer 328, such as during start-up, is typically stored in ROM. The RAM typically contains data and/or program modules that are immediately accessible to and/or presently being operated on by the processing unit. By way of example, and not limitation, the computer 328 also comprises an operating system, application programs, other program modules, and program data.

The components shown in the memory may also be included in other removable/nonremovable, volatile/nonvolatile computer storage media. For example only, a hard disk drive may read from or writes to nonremovable, nonvolatile magnetic media, a magnetic disk drive may read from or writes to a removable, nonvolatile magnetic disk, and an optical disk drive may reads from or writes to a removable, nonvolatile optical disk such as a CD ROM or other optical media. Other removable/nonremovable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The drives and their associated computer storage media discussed above and illustrated in FIG. 3, provide storage of computer-readable instructions, data structures, program modules and other data for the computer 328.

In operation, the apparatus thus described may be used to determine the acoustic velocity, and other physical properties, of various fluids in chamber 300 up to about 400° F. and 25,000 psi with improved accuracy over conventional tools. The various fluids include, but are not limited to, reservoir hydrocarbons and other types of miscible fluids and multiphase immiscible fluids. If a single-phase miscible fluid is preferred, either reflector 316 or 416 may be used to mix or agitate the fluid sample as necessary to maintain a homogenous solution. This may be accomplished using two independently driven electromagnetic coils. For example, a first coil 340 and a second coil 342 are used in the embodiment illustrated in FIG. 3. Each coil 340 and 342 separately circumscribe chamber 300 to form at least one complete loop. Each coil 340 and 342 may be coupled with a power source using cable 330, which may be the same power source used to drive the transducer 312. By alternating power to each coil 340 and 342, the reflector 316 or 416 may be manipulated within chamber 300 due to the material properties of the reflector. The process of repeatedly manipulating the reflector is thus, used to mix the fluid sample. The manipulation of the reflector may also be used in determining the volume, viscosity and bubble point pressure of the fluid sample as described further in reference to FIG. 5.

Figure 5:
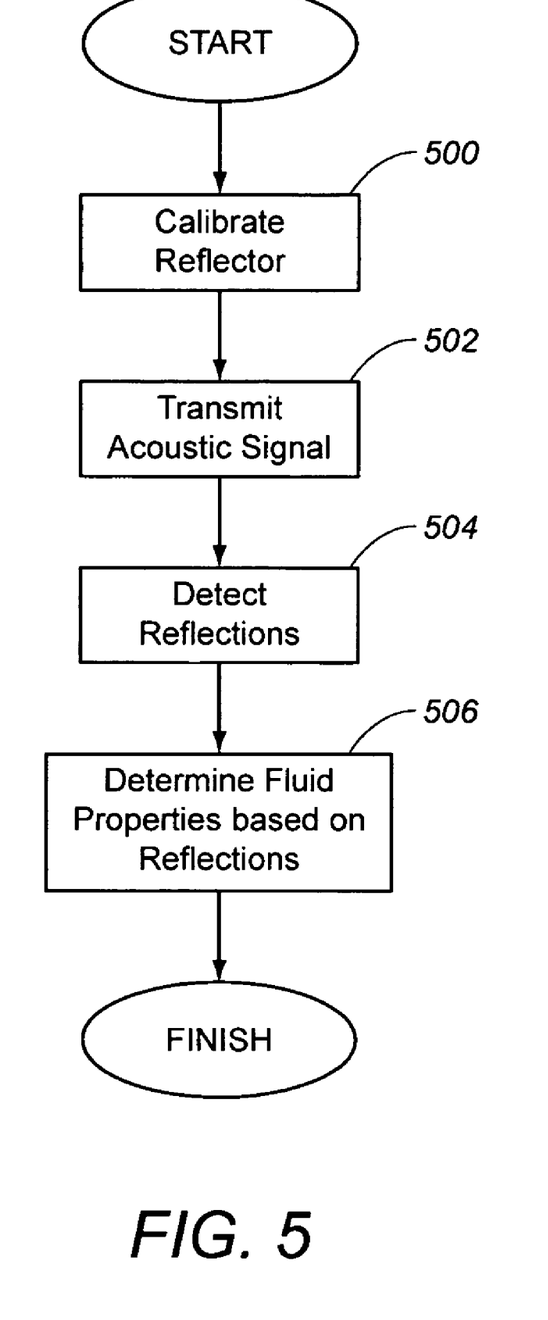
FIG. 5 is a flowchart illustrating one method of the present invention.

A flowchart in FIG. 5 illustrates one embodiment of a method for operating the apparatus described in reference to FIG. 3. In step 500, the distance (D) between the first reflective surface 318 and the second reflective surface 320 may be calibrated based upon a known coefficient of thermal expansion for the material comprising the reflector 316 at a predetermined temperature and pressure of the fluid sample in chamber 300. This distance (D), however, may not need to be calibrated depending on the material comprising the reflector 316 or 416.

In step 502, the transducer 312 transmits an acoustic signal. As the signal leaves the transducer 312, it radiates in multiple directions as it moves through the fluid in chamber 300. Path 332 defines movement of the acoustic signal as it leaves the transducer 312 and is reflected off of the first reflective surface 318 and returns to the transducer 312. Path 334 defines movement of the acoustic signal as it leaves the transducer 312 and is reflected off of the second reflective surface 320 and returns to the transducer 312. Path 336 defines movement of the acoustic signal as it passes through opening 322 and is reflected off of piston 304 and returns to the transducer 312. In each case, the reflector 316 is substantially stationary, however, may be moved away from path 336 as explained below.

As the acoustic signal travels along paths 332, 334, and 336, the reflections of the acoustic signal are detected by the transducer 312 in step 504. Based upon the time of flight it takes for the acoustic signal to traverse each path 332, 334, and 336, the acoustic velocity, volume and density of the fluid sample in chamber 300 may be determined in step 506.

The acoustic velocity of the fluid sample in chamber 300 may be determined at a predetermined temperature and pressure (Vel.$_{T,P}$) by:

$$\text{Vel.}_{T,P} = D_{T,P} \div 0.5 \times (T_2 - T_1)$$

where $D_{T,P}$ is the calibrated distance (D) at the fluid sample temperature and pressure; $T_2$ is the time of flight for the acoustic signal to travel along path 334; and $T_1$ is the time of flight for the acoustic signal to travel along path 332. This calculation may be repeated using multiple signals, resulting in a repetitive acoustic wave, for more accurate results. The oscilloscope 326 displays an image of the detected reflections, making $T_2$ and $T_1$ easily determinable by use of the oscilloscope 326 and/or computer 328. Acoustic velocity measurements of water using this method have been discovered to agree to within ±0.5% of acoustic velocities quoted in the *AGU Reference of Physical Constants*.

Once the acoustic velocity (Vel.$_{T,P}$) is known, the fluid sample volume at the predetermined temperature and pressure (Vel.$_{T,P}$) is determined by:

$$\text{Vol.}_{T,P} = (0.5 \times T_3 \times Vel._{T,P}) \times (\pi \times R^2)$$

where $T_3$ is the time of flight for the acoustic signal to traverse path 336, and R is the piston radius. In order to reduce the possibility of error when measuring $T_3$, the reflector 316 or 416 should be positioned away from path 336. For example, any surface of the reflector 316 or 416 that obstructs path 336 may produce erroneous results for $T_3$. This may be accomplished by moving the chamber 300 and/or charging the first coil 340 to attract the reflector 316 or 416 away from path 336.

Once the fluid sample volume (Vol.$_{T,P}$) is known, the density of the fluid sample at the predetermined temperature and pressure (Den.$_{T,P}$) is determined by:

$$\text{Den.}_{T,P} = M \div \text{Vol.}_{T,P}$$

where M is the known mass of the fluid sample in chamber 300. Additional reflective surfaces may be used to measure the time of flight ($T_N$) for an acoustic signal in each phase of an immiscible fluid sample and/or to test homogeneity.

Viscosity, a fluids resistance to flow, may also be determined using the first coil 340 and the second coil 342. In step 506, for example, the reflector 316 or 416 may be manipulated between a predetermined first position and a predetermined second position in the chamber 300 by alternating power between the first coil 340 and second coil 342. As the reflector 316 or 416 moves within chamber 300 due to the magnetic forces imposed by the first coil 340 and the second coil 342, the distance between the first predetermined position and the second predetermined position will become apparent to those skilled in the art of using an oscilloscope. The time it takes for the reflector 316 or 416 to move between the first position and the second position is determined by the difference ($\Delta T$) between a time of flight for an acoustic signal to reflect off of the reflector 316 or 416 and return to the transducer 312 at the first position and at the second position. The velocity of the reflector 316 or 416 as it moves through the fluid is therefore, the distance between the first position and the second position of the reflector 316 or 416 divided by $\Delta T$. The viscosity of the fluid may be determined from the velocity of the reflector 316 or 416 and its known physical properties using techniques well known in the art. This technique provides an improved viscosity profile without the necessity of complex and expensive timing circuitry. Moreover, this technique may be performed at in situ locations that may otherwise preclude the use of complex lab equipment.

The foregoing apparatus and methods for determining various physical properties of the fluid sample in chamber 300 were experimentally tested as further described in the following example.

EXAMPLE 1

In this example, the apparatus described in reference to FIG. 3 was used in a laboratory set-up to analyze a crude oil fluid sample having a mass of 49.8710 grams at a temperature of 242° F. The chamber containing the crude oil sample was subjected to various pressures as shown in Table 1 below, each pressure (Column 1) being represented in pounds per square inch. At each pressure, an acoustic signal was transmitted through the crude oil sample and reflections of the acoustic signal off of the reflector (ring) and piston were detected, recorded and used to compile Table 1. The velocity of the acoustic signal in the crude oil sample at each pressure ($Vel._{T,P}$) is represented in feet per second (Column 2); the density of the crude oil sample at each pressure ($Den._{T,P}$) is represented in grams per cubic centimeter (Column 3); and the volume of the crude oil sample at each pressure ($Vol._{T,P}$) is represented in cubic centimeters (Column 10). The distance (D) is 1.503 inches, which represents the distance between the first reflective surface and the second reflective surface. $T_1$ $_{and}$ $_{T2}$ are represented by the ring top (Column 6) and the ring bottom (Column 7), respectively, in microseconds. $T_3$ is represented by the piston (Column 8), also in microseconds. The cylinder position (Column 9) represents the distance, in inches, between piston 304 and the transducer 312, which is based upon the corresponding pressure and velocity figures in Columns 1 and 2. The cylinder position is used to determine the crude oil sample volume, which was adjusted using a volume correction factor of 9.4136 c.c. at each pressure.

Based upon the velocity, volume and/or density of a crude oil sample at a predetermined temperature and pressure, its compressibility and adiabatic compressibility may also be determined. The compressibility of a crude oil sample is a fundamental component in determining reservoir quality. Applying pressure to a crude oil sample reduces its volume. Conversely, the application of pressure to a crude oil sample will increase its density as reflected in Table 1.

TABLE 1

| Column 1 psi | Column 2 Velocity (ft/sec) | Column 3 Density (gm/cc) | Column 4 Compressibility (dV/dpsi)1/Vo | Column 5 Adiabatic Compressibility (1/psi) | Column 6 Ring Top (usec) | Column 7 Ring Bottom (usec) | Column 8 Piston (usec) | Column 9 Cyl. Position (in.) | Column 10 Volume (cc) |
|---|---|---|---|---|---|---|---|---|---|
| 19951 | 5205 | 0.7445 | 3.91E−06 | 3.67E−06 | 91.68 | 139.6 | 142.9 | 4.4760 | 66.9845 |
| 19054 | 5132 | 0.7416 | 4.20E−06 | 3.79E−06 | 93.76 | 142.4 | 145.8 | 4.4966 | 67.2498 |
| 17922 | 5035 | 0.7376 | 4.51E−06 | 3.96E−06 | 96.64 | 147.1 | 149.6 | 4.5245 | 67.6083 |
| 16981 | 4952 | 0.7342 | 4.84E−06 | 4.11E−06 | 99.28 | 149.7 | 153.2 | 4.5494 | 67.9289 |
| 16023 | 4865 | 0.7304 | 5.22E−06 | 4.29E−06 | 102 | 153.3 | 157 | 4.5767 | 68.2795 |
| 14981 | 4766 | 0.7260 | 5.67E−06 | 4.49E−06 | 105.5 | 157.7 | 161.6 | 4.6088 | 68.6925 |
| 14072 | 4675 | 0.7219 | 6.18E−06 | 4.69E−06 | 108.6 | 161.9 | 165.8 | 4.6392 | 69.0840 |
| 13019 | 4566 | 0.7167 | 6.81E−06 | 4.96E−06 | 112.6 | 167.2 | 171.3 | 4.6778 | 69.5802 |
| 11973 | 4452 | 0.7112 | 7.56E−06 | 5.25E−06 | 117 | 174.1 | 177.2 | 4.7203 | 70.1268 |
| 11063 | 4348 | 0.7058 | 8.44E−06 | 5.55E−06 | 121.4 | 178.7 | 183 | 4.7613 | 70.6549 |
| 9995 | 4218 | 0.6990 | 9.59E−06 | 5.96E−06 | 126.9 | 187 | 190.2 | 4.8155 | 71.3511 |
| 8946 | 4081 | 0.6914 | 1.11E−05 | 6.43E−06 | 134.4 | 195.3 | 198.9 | 4.8765 | 72.1357 |
| 7995 | 3948 | 0.6836 | 1.26E−05 | 6.95E−06 | 141 | 204.2 | 207.9 | 4.9404 | 72.9578 |

Compressibility (Column 4) is determined by:

$$\text{Com.} = (Vol._{T,P1} - Vol._{T,P2}) \div (P_1 - P_2 \times 1 Vol._{T,P1})$$

where $Vol._{T,P1}$ is the initial volume of the crude oil sample at a predetermined temperature (T) and pressure ($P_1$); $Vol._{T,P2}$ is the volume of the crude oil sample at the same temperature (T) but a different pressure. ($P_2$). Adiabatic compressibility (Column 5) may also be useful for reservoir management and is determined by:

$$\text{Com.} = \sqrt{Vel._{T,P} \div Den._{T,P}}$$

where $Vel._{T,P}$ and $Den._{T,P}$ have been previously calculated. Power law adjustments were applied to the data illustrated in Table 1 in order to render a linear plot of the data. The results, illustrated by this example and others, reveal that the apparatus and techniques used herein to determine density ($Den._{T,P}$) are more accurate than measurements of density using a pycnometer, which was determined to include a margin of error of about −0.39%

The bubble point pressure, representing the pressure at which a gas bubble begins to form on top of a crude oil sample containing dissolved gases, plays a significant role in reservoir management. For example, crude oil samples obtained at pressures below the bubble point pressure often yield greater volumes of gas than crude oil. The bubble point pressure may be measured by compressing a crude oil sample to a pressure above its bubble point and then slowly reducing its pressure and observing (visually or by using compressibility results) when and where gas bubbles begin to form. Because an accurate bubble point pressure may only be determined by agitating or mixing the crude oil sample, the apparatus described in reference to FIG. 3 and its in situ applications are well suited for bubble point pressure measurements.

The present invention therefore, provides an accurate and efficient determination of fluid properties for fluid characterization and quantitative interpretation without requiring calibration due to dynamic chamber dimensions. Those skilled in the art of oil and gas exploration will appreciate that the in situ application of the present invention may be used for quantitative interpretation of seismic activities, such as amplitude calibrations and estimates of hydrocarbon potential. Other benefits that will be apparent include:

i) contemporaneous analysis with fluid sample extraction;
ii) no dependency on handling, transport and export;
iii) more accurate determination of compositional gradients due to fluid characterization at closer intervals;
iv) cleaner samples as a result of more accurate correction for mud filtrate invasion on formation fluid sample measurements;
v) input for gassmann fluid substitution equations;
vi) determination of when the fluid samples are clean enough for testing;
vii) monitoring dependency of fluid sample on temperature and pressure, which may contain important information for 4D calibrations;
viii) measurement of acoustic properties at reservoir temperature as a function of decreasing pressure, which provides an excellent estimate of the bubble point pressure of crude oil;
ix) immediate detection of heavy component (asphaltene) dropout thus, preventing costly analysis on altered samples;
x) synergy with other results from optical, acoustical, olfactory, capillary pressure and NMR devices;
xi) potential viscosity and permeability measurements; and
xii) restoration of the fluid sample to its in situ state, if necessary, and comparison of the in situ state with its restoration properties.

The present invention, as described in reference to FIG. 3, may be easily incorporated into the design of the fluid sampling device illustrated in FIGS. 1 and 2. Referring to FIG. 2, the accumulation chamber 30 comprises a cylinder wall 42 that encloses a cylindrical volume 50 between opposite cylinder and plugs 47 and 49. Within the cylindrical volume 50 are two free pistons 54 and 56. The free pistons 54 and 56 divide the cylindrical volume 50 into three variable volume chambers 60, 62, and 64.

The formation sample chamber 64 may, for example, communicate with a valve control formation fluid transfer conduit 70 from the formation pump 19 that is connected through the cylinder in plug 47. An agitation ball 55 is placed in sample chamber 64 upon final assembly. The wellbore chamber 60 may receive a conduit 76 having an uncontrolled reversible flow communication with the wellbore annulus. The intermediate chamber 62 between the pistons 54 and 56 may be charged with a suitable gas through conduit 86 and the piston 54. The conduit 86 includes a check valve 88 in series with a valve or plug 89 set within a piston boss 58.

The cylinder end plugs 47 and 49 make a sealed interface with respective retainer sleeve 68 and 69. The end plug 49 is removed from the cylinder end for connection access to the piston conduit 86. When the intermediate volume 62 is charged with gas, the gas pressure drives the pistons 54 and 56 against the opposite limits sleeve 68 and 69. When the gas charge is complete, the charging conduit is removed from the piston conduit 86. The check valve 88 prevents an exhaust flow of gas from the volume 62 until the conduit 86 is secured by the valve 89. The cylinder sample chamber 64 is finally closed by assembling the end plug 49. The end plug is penetrated by the wellbore fluid conduit 76.

The mixing ball 55 in FIG. 2 may be replaced with the reflector 316 in FIG. 3. The transducer 312 may be positioned on the piston 56 in FIG. 2 or the plug 47 in FIG. 2. Alternatively, a separate transmitter and receiver may be positioned on the piston 56 or the plug 47, respectively, or vice versa. Nominal modifications to the plug 47 and/or the piston 56 may be necessary and apparent to those of ordinary skill in the art. The remainder of the sampling tool illustrated in FIG. 2 may be modified by linking the pulsar/receiver 324 with the cable 12 in FIG. 1 to transmit acoustic data from the transducer 312 up the wellbore to the surface for review and analysis. Accordingly, the device illustrated in FIG. 2 already provides a means for maintaining the fluid sample in chamber 64 at in situ conditions thus, requiring only slight modifications to incorporate the necessary components for determining various acoustic properties of the fluid sample in chamber 64. Additionally, the servo motor 310 may be eliminated, and the piston 304 and chamber 300 may not need to be insulated.

In summary, the present invention permits real-time characterization of fluid properties in a variety of applications at in situ conditions. The present invention has therefore, been described in relation to particular embodiments, which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects set forth above, together with other advantages, which are obvious and inherent to the apparatus and method. It will be understood that certain features and sub-combinations are of utility and may be employed without reference to other features and sub-combinations. This is contemplated and within the scope of the claims.

The invention claimed is:

1. An apparatus for acoustically analyzing a fluid comprising:
   a chamber for holding the fluid;
   a transmitter positioned within the chamber for transmitting an acoustic signal through the fluid in said chamber;
   a reflector positioned within the fluid for reflecting the acoustic signal through the fluid in said chamber;
   a receiver positioned within the chamber for detecting a reflection of the acoustic signal; and
   first and second electromagnetic coils, the first electromagnetic coil and the second electromagnetic coil being independently driven for manipulating the reflector;
   wherein said apparatus is incorporated in a downhole sampling device; and
   wherein the acoustic signal that is detected does not leave the chamber before detection.

2. The apparatus of claim 1, wherein the chamber comprises a sealed first end, a piston slidably disposed within a second end of the chamber and a conduit for introducing the fluid into the chamber.

3. The apparatus of claim 2, further comprising a servo-motor for driving the piston and varying at least one of a pressure and a temperature of the fluid within the chamber.

4. The apparatus of claim 1, wherein the chamber is thermally insulated to substantially maintain at least one of a pressure and temperature of the fluid within the chamber.

5. The apparatus of claim 1, wherein the transmitter and the receiver are embodied in a single piezoelectric transducer.

6. The apparatus of claim 5, further comprising a piston mounted within the chamber near the first end for supporting the transducer within the fluid.

7. The apparatus of claim 6, further comprising a square-wave pulsar/receiver connected to the transducer for driving the transducer and processing the reflection of the acoustic signal.

8. The apparatus of claim 7, further comprising an oscilloscope connected to the square-wave pulsar/receiver for imaging the reflection of the acoustic signal.

9. The apparatus of claim 8, wherein the reflector is a disc positioned opposite the transducer relative to the piston.

10. The apparatus of claim 8, wherein the reflector is a ring positioned opposite the transducer relative to the piston.

11. The apparatus of claim 6, wherein the piston is a static piston.

12. The apparatus of claim 1, wherein the reflector comprises at least one of a first reflective surface and a second reflective surface for analyzing a property of the fluid comprising at least one of velocity, volume, density, compressibility and viscosity.

13. The apparatus of claim 12, wherein the reflector comprises a material having a substantially low coefficient of thermal expansion and a high bulk modulus for mitigating any variation in a distance between the first reflective surface and the second reflective surface as the material is subjected to a predetermined temperature and pressure within the chamber.

14. The apparatus of claim 1, wherein the downhole sampling device forms part of a wireline fluid sampling tool.

15. The apparatus of claim 1, wherein the reflector is moveably positioned.

16. An apparatus for acoustically analyzing a fluid comprising:
a chamber for holding the fluid;
a transducer coupled with the chamber for transmitting an acoustic signal through the fluid in said chamber and detecting a reflection of the acoustic signal;
a reflector positioned within the fluid for reflecting the acoustic signal through said fluid;
first and second electromagnetic coils, the first electromagnetic coil and second electromagnetic coil being independently driven for manipulating the reflector; and
a first piston mounted within the chamber for supporting the transducer within the fluid.

17. The apparatus of claim 16, wherein the chamber comprises a sealed first end, a second piston slidably disposed within a second end of the chamber and a conduit for introducing the fluid into the chamber.

18. The apparatus of claim 16, wherein the reflector comprises at least one of a first reflective surface and a second reflective surface for analyzing a property of the fluid comprising at least one of velocity, volume, density, compressibility, and viscosity.

19. The apparatus of claim 18, wherein the reflector comprises a material having a substantially low coefficient of thermal expansion and a high bulk modulus for mitigating any variation in a distance between the first reflective surface and the second reflective surface as the material is subjected to a predetermined temperature and pressure within the chamber.

20. The apparatus of claim 16, wherein the reflector is moveably positioned.

21. The apparatus of claim 16, wherein the transducer is embodied in a single piezoelectric transducer.

22. The apparatus of claim 16, further comprising a square-wave pulsar/receiver connected to the transducer for driving the transducer and processing the reflection of the acoustic signal.

23. The apparatus of claim 22, further comprising an oscilloscope connected to the square-wave pulsar/receiver for imaging the reflection of the acoustic signal.

24. The apparatus of claim 23, wherein the reflector is a disc positioned opposite the transducer relative to the piston.

25. The apparatus of claim 23, wherein the reflector is a ring positioned opposite the transducer relative to the piston.

26. The apparatus of claim 16, wherein the first piston is a static piston.

27. A method for acoustically analyzing a fluid in a chamber using a transmitter, a substantially stationary reflector positioned within the fluid inside the chamber, and a receiver, all incorporated in a downhole sampling device, the method comprising the steps of:
drawing a formation fluid from an earth formation; and
under in-situ conditions:
transmitting an acoustic signal from the transmitter through the fluid in the chamber; and
detecting reflections of the acoustic signal from the reflector at the receiver;
wherein the acoustic signal that is detected does not leave the chamber before detection; and
wherein the velocity of the acoustic signal through the fluid at a predetermined temperature and pressure ($\text{Vel.}_{T,P}$) is determined by:

$$\text{Vel.}_{T,P} = D_{T,P} \div 0.5 \times (T_2 - T_1).$$

28. The method of claim 27, wherein the transmitter and the receiver are embodied in a single piezoelectric transducer.

29. The method of claim 28, wherein the transducer is supported within the fluid at one end of the chamber.

30. The method of claim 29, wherein the reflector is a disc positioned opposite the transducer relative to another end of the chamber.

31. The method of claim 29, wherein the reflector is a ring positioned opposite the transducer relative to another end of the chamber.

32. The method of claim 27, further comprising the step of determining a property of the fluid comprising at least one of velocity, volume, density, compressibility, and viscosity.

33. The method of claim 32, wherein the reflector is moveably positioned.

34. The method of claim 27, wherein the volume of the fluid at the predetermined temperature and pressure ($\text{Vol.}_{T,P}$) is determined by:

$$\text{Vol.}_{T,P} = (0.5 \times T_3 \times \text{Vel}_{T,P}) \times (\pi \times R^2).$$

35. The method of claim 34, wherein the density of the fluid at the predetermined temperature and pressure ($\text{Den}_{T,P}$) is determined by:

$$\text{Den.}_{T,P} = M \div \text{Vol.}_{T,P}.$$

36. The method of claim 27, wherein the predetermined temperature is about 400° F. and the predetermined pressure is about 25,000 psi.

37. The method of claim 27, further comprising the step of calibrating the reflector based upon a known coefficient of thermal expansion for a material comprising the reflector.

38. The method of claim 27, wherein the reflector is substantially stationary.

39. The method of claim 27, wherein the reflector is moveably positioned.

40. An apparatus for acoustically analyzing a fluid comprising:
a chamber for holding the fluid;
a transmitter positioned within the chamber for transmitting an acoustic signal through the fluid in said chamber;
a reflector positioned within the fluid for reflecting the acoustic signal through the fluid in said chamber; and
a receiver positioned within the chamber for detecting a reflection of the acoustic signal;
wherein said apparatus is incorporated in a downhole sampling device;
wherein the acoustic signal that is detected does not leave the chamber before detection; and
wherein the reflector comprises a first reflective surface and a second reflective surface, defining a first path of movement of the acoustic signal through the fluid as the acoustic signal leaves the transmitter and is reflected off of the first reflective surface to the receiver, and defining a second path of movement of the acoustic signal through the fluid as the acoustic signal leaves the transmitter and is reflected off of the second reflective surface to the receiver, whereby the second path through the fluid is longer than the first path through the fluid.

41. An apparatus for acoustically analyzing a fluid comprising:
a chamber for holding the fluid;
a transducer coupled with the chamber for transmitting an acoustic signal through the fluid in said chamber and detecting a reflection of the acoustic signal;
a reflector positioned within the fluid for reflecting the acoustic signal through said fluid; and
a first piston mounted within the chamber for supporting the transducer within the fluid;
wherein the reflector comprises a first reflective surface and a second reflective surface, defining a first path of movement of the acoustic signal through the fluid as the acoustic signal leaves the transducer and is reflected off of the first reflective surface and returns to the transducer, and defining a second path of movement of the acoustic signal through the fluid as the acoustic signal leaves the transducer and is reflected off of the second reflective surface and returns to the transducer, whereby the second path through the fluid is longer than the first path through the fluid.

42. An apparatus for acoustically analyzing a fluid comprising:
a chamber for holding the fluid;
a transmitter positioned within the chamber for transmitting an acoustic signal through the fluid;
a reflector positioned within the fluid for reflecting the acoustic signal; and
a receiver positioned within the chamber for detecting a reflection of the acoustic signal,
wherein the reflector comprises at least one of a first reflective surface and a second reflective surface for analyzing a property of the fluid comprising at least one of velocity, volume, density, compressibility and viscosity, and wherein the reflector comprises a material having a substantially low coefficient of thermal expansion and a high bulk modulus for mitigating any variation in a distance between the first reflective surface and the second reflective surface as the material is subjected to a predetermined temperature and pressure within the chamber.

43. The apparatus of claim 42, wherein the reflector is moveably positioned.

44. The apparatus of claim 43, further comprising a first electromagnetic coil and a second electromagnetic coil, the first electromagnetic coil and the second electromagnetic coil being independently driven for manipulating the reflector.

45. An apparatus for acoustically analyzing a fluid comprising:
a chamber for holding the fluid;
a transmitter positioned within the chamber for transmitting an acoustic signal through the fluid;
a reflector positioned within the fluid for reflecting the acoustic signal; and
a receiver positioned within the chamber for detecting a reflection of the acoustic signal;
wherein the reflector comprises a first reflective surface and a second reflective surface, defining a first path of movement of the acoustic signal through the fluid as the acoustic signal leaves the transmitter and is reflected off of the first reflective surface to the receiver, and defining a second path of movement of the acoustic signal through the fluid as the acoustic signal leaves the transmitter and is reflected off of the second reflective surface to the receiver, whereby the second path through the fluid is longer than the first path through the fluid.

46. The apparatus of claim 45, wherein the reflector is moveably positioned.

47. The apparatus of claim 46, wherein the transmitter and the receiver are embodied in a single transducer.

48. A method for acoustically analyzing a fluid in a chamber using a transmitter, a reflector positioned within the fluid inside the chamber, and a receiver, the method comprising the steps of:
transmitting an acoustic signal from the transmitter through the fluid;
detecting reflections of the acoustic signal from the reflector at the receiver; and
determining a property of the fluid comprising at least one of velocity, volume, density, compressibility, and viscosity, wherein the velocity of the acoustic signal through the fluid at a predetermined temperature and pressure ($\text{Vel}_{T,P}$) is determined by:

$$\text{Vel.}_{T,P} = D_{T,P} \div 0.5 \times (T_2 - T_1).$$

49. The method of claim 48, wherein the volume of the fluid at the predetermined temperature and pressure ($\text{Vol}_{T,P}$) is determined by:

$$\text{Vol.}_{T,P} = (0.5 \times T_3 \times \text{Vel.}_{T,P}) \times (\pi \times R^2).$$

50. The method of claim 49, wherein the density of the fluid at the predetermined temperature and pressure ($\text{Den.}_{T,P}$) is determined by:

$$\text{Den.}_{T,P} = M \div \text{Vol.}_{T,P}.$$

51. The method of claim 48, wherein the predetermined temperature is about 400° F. and the predetermined pressure is about 25,000 psi.

52. The method of claim 48, further comprising the step of calibrating the reflector based upon a known coefficient of thermal expansion for a material comprising the reflector.

53. The method of claim 48, wherein the transmitter and the receiver are embodied in a transducer.

54. The method of claim 48, wherein the transmitter and the receiver are embodied in a single piezoelectric transducer.

55. The method of claim 48, wherein the reflector is moveably positioned.

56. The method of claim 55, further comprising the step of manipulating the reflector by independently driving a first electromagnetic coil and a second electromagnetic coil.

57. An apparatus for acoustically analyzing a fluid comprising:
   a chamber for holding the fluid;
   a transmitter positioned within the chamber for transmitting an acoustic signal through the fluid in said chamber;
   a reflector positioned within the fluid for reflecting the acoustic signal; and
   a receiver positioned within the chamber for detecting a reflection of the acoustic signal;
   wherein the chamber comprises a sealed first end, and a piston slidably disposed within a second end of the chamber and a motor coupled to the piston for driving the piston and varying at least one of a pressure and a temperature of the fluid within the chamber.

58. The apparatus of claim 57, further comprising a conduit for introducing the fluid into the chamber.

59. The apparatus of claim 58, wherein the motor is a servomotor.

60. The apparatus of claim 57, wherein the chamber is thermally insulated to substantially maintain at least one of a pressure and temperature of the fluid within the chamber.

61. The apparatus of claim 57, wherein the transmitter and the receiver are embodied in a transducer.

62. The apparatus of claim 61, further comprising a square-wave pulsar/receiver connected to the transducer for driving the transducer and processing the reflection of the acoustic signal.

63. The apparatus of claim 57, wherein the transmitter and the receiver are embodied in a single piezoelectric transducer.

64. The apparatus of claim 57, further comprising a static piston mounted within the chamber near the first end.

65. The apparatus of claim 64, wherein the transmitter and the receiver are embodied in a single piezoelectric transducer that is supported on the static piston.

66. The apparatus of claim 57, herein the transmitter and the receiver are embodied in a single piezoelectric transducer that is supported on the slidably disposed piston.

* * * * *